United States Patent [19]

Sallmann et al.

[11] 4,296,128

[45] Oct. 20, 1981

[54] CARBOXYLIC ACID HYDRAZIDES AND PROCESSES FOR THEIR MANUFACTURE

[75] Inventors: Alfred Sallmann; Richard Göschke, both of Bottmingen, Switzerland

[73] Assignee: Ciba-Geigy Corporation, Ardsley, N.Y.

[21] Appl. No.: 147,458

[22] Filed: May 7, 1980

[30] Foreign Application Priority Data

May 11, 1979 [CH] Switzerland .................. 4416/79

[51] Int. Cl.³ .................. C07C 149/43; A61K 31/24; A61K 31/195
[52] U.S. Cl. .................. 424/309; 560/17; 562/431; 424/319
[58] Field of Search .................. 560/17; 562/431; 424/309, 319

[56] References Cited

U.S. PATENT DOCUMENTS 2,700,671  1/1955  Hafliger .................. 560/17

FOREIGN PATENT DOCUMENTS 1814649  6/1970  Fed. Rep. of Germany.
2023415  11/1971  Fed. Rep. of Germany.
974743  11/1964  United Kingdom.

OTHER PUBLICATIONS

Pfister, Helv. Chim. Acta, 44 pp. 232-237 (1961).
Wilson, "Textbook of Organic Medical and Pharmaceutical Chemistry," pp. 39, 40 & 50 (1954), RS 403W7.

*Primary Examiner*—Robert Gerstl
*Assistant Examiner*—Michael L. Shippen
*Attorney, Agent, or Firm*—Norbert Gruenfeld

[57] ABSTRACT

New carboxylic acid hydrazides of the formula

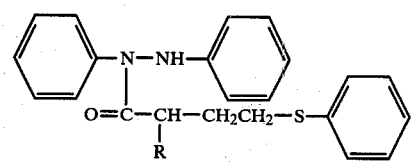

in which
R represents an optionally esterified carboxy group, and salts of the compound of the formula I, in which R represents carboxy, possess antithrombotic properties and can be used as medicinal active substances in pharmaceutical preparations.

3 Claims, No Drawings

CARBOXYLIC ACID HYDRAZIDES AND PROCESSES FOR THEIR MANUFACTURE

The invention relates to new carboxylic acid hydrazides of the formula

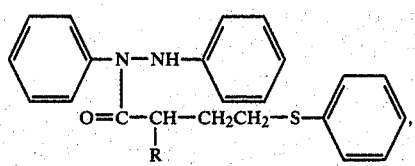

in which R represents an optionally esterified carboxy group, and salts of the compound of the formula I, in which R is carboxy, processes for the manufacture of the new compounds, pharmaceutical preparations containing them and their use as medicinal active substances.

Esterified carboxy R is, for example, carboxy esterified with an alcohol of an aliphatic nature, such as optionally substituted lower alkoxycarbonyl, for example lower alkoxycarbonyl, hydroxy-lower alkoxycarbonyl or lower-alkoxy-lower alkoxycarbonyl or phenyl-lower alkoxycarbonyl optionally substituted in the phenyl moiety for example by lower alkyl, lower alkoxy, halogen and/or trifluoromethyl.

The term "lower" organic radicals and compounds shall mean, for example, those having up to 7 and especially up to 4 C-atoms. Moreover:

Lower alkoxycarbonyl is, for example, methoxycarbonyl, ethoxycarbonyl, propoxycarbonyl, isopropoxycarbonyl or butoxycarbonyl, isobutoxycarbonyl, secondary butoxycarbonyl or tertiary butoxycarbonyl, also pentyloxycarbonyl, hexyloxycarbonyl or heptyloxycarbonyl.

Hydroxy-lower alkoxycarbonyl may have 1 or 2 hydroxy groups and is preferably hydroxy-lower alkoxycarbonyl in which the hydroxy group(s) is(are) bonded in a position higher than the 1-position, for example 2-hydroxyethoxycarbonyl, 2- or 3-hydroxypropoxycarbonyl or 2,3-dihydroxypropoxycarbonyl.

Lower alkoxy-lower alkoxycarbonyl is, for example, lower alkoxy-lower alkoxycarbonyl in which the terminal lower alkoxy group is bonded in a position higher than the 1-position, for example 2-methoxyethoxycarbonyl or 2-ethoxyethoxycarbonyl or 3-methoxypropoxycarbonyl or 3-ethoxypropoxycarbonyl.

Lower alkyl is, for example methyl, ethyl, propyl, isopropyl, butyl, secondary butyl, isobutyl or tertiary butyl, furthermore pentyl, hexyl or heptyl.

Lower alkoxy is, for example, methoxy, ethoxy, propoxy, isopropoxy, butoxy, isobutoxy, secondary butoxy or tertiary butoxy, furthermore pentyloxy, hexyloxy or heptyloxy.

Halogen is, for example, halogen of an atomic number up to and including 35, such as fluorine, chlorine or bromine.

Phenyl-lower alkoxycarbonyl is, for example, benzyloxycarbonyl, 2-phenylethoxycarbonyl or 3-phenylpropoxycarbonyl.

Salts of the compound of the formula I, in which R is carboxy, are, for example, pharmaceutically useful salts with bases, such as pharmaceutically useful metal or ammonium salts. Pharmaceutically useful metal salts are, for example, alkali metal or alkaline earth metal salts, for example lithium, sodium, potassium, magnesium or calcium salts, also zinc, iron or copper salts. Pharmaceutically useful ammonium salts are, for example, ammonium salts with ammonia or amines, such as optionally C-substituted, for example C-hydroxylated or C-aminated lower alkylamines, for example with di- or triethylamine, dimethylamine, 2-hydroxy-1,1-bis(hydroxymethyl)ethylamine, triethanolamine, ethylenediamine or guanidine, furthermore ammonium salts with cyclic organic amines such as piperidine, piperazine, N'-methylpiperazine or morpholine.

The compounds of the formula I and their pharmaceutically useful salts possess valuable pharmaceutical properties. Thus, it has been shown that, in a series of experiments for demonstrating an antithrombotic action, especially in cyclooxygenase-dependent tests, they possess a marked antithrombotic activity. This can be demonstrated for example in vivo using the Arthus reaction, see Brit. J. Pharmacology, 57, p. 441 (1976), in the dosage range of from approximately 5 to 100 mg/kg p.o. and in rabbits by means of their inhibiting action on pulmonary embolism induced by arachidonic acid, see Pharmacology, 14, 522 (1976), in the dosage range of from approximately 0.3 to 20 mg/kg p.o., and also in vitro by means of the inhibition of prostaglandin synthesis from arachidonic acid by prostaglandin synthetase, demonstrated in the experiment series according to Prostaglandin, 7, 123 (1974) in a concentration in the range from 75 to 1500 mg/liter.

The compounds of the formula I and their pharmaceutically useful salts are accordingly excellently suitable for the treatment of cardiovascular disorders, especially for the treatment of thrombotic disorders, especially of conditions in which an abnormal function of the blood platelets is the causative or an accompanying factor, for example in cardiac infarction patients for the prevention of a sudden death, and may accordingly be used as active substance in antithrombotic medicaments.

The invention relates especially to compounds of the formula I in which R represents carboxy, lower alkoxycarbonyl, for example having up to 5 C-atoms, for example methoxycarbonyl or ethoxycarbonyl, or phenyl-lower alkoxycarbonyl, for example having up to 11 C-atoms, for example benzyloxycarbonyl or 2-phenylethoxycarbonyl, and salts of the compound of the formula I, in which R represents carboxy, namely the 2-(2-phenylthioethyl)malonic acid N,N'-diphenyl hydrazide and salts thereof.

The compounds of the formula I can be prepared in accordance with methods known per se, for example as follows: in a compound of the formula

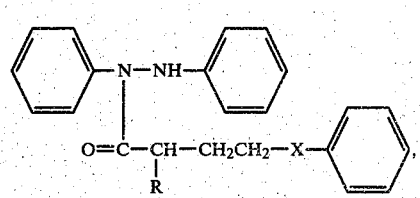

in which
X represents a radical that can be converted into the thio group by reduction, wherein the secondary nitrogen atom and/or a carboxy group R may be present in an intermediately protected form, X is reduced to the thio group, if required in the compound which may be obtained according to the process the protecting group(s) is(are) split off, and, if desired, the resulting compound is converted into a different compound of the formula I, and/or the optionally resulting compound of the formula I, in which R is carboxy, is converted into a salt, or a resulting salt of such a compound is converted into the free acid or into a different salt. The radical X which can be converted into the thio group by reduction is especially the sulphinyl group of the formula —S(O)—, also the sulphonyl group of the formula —(S)O—.

The reduction is carried out in the customary manner, for example by treating with a selective reducing agent known from literature as suitable for analogous reductions, advantageously in an organic solvent, if required whilst cooling or heating, for example in a temperature range of from approximately 0° to 100° C., and/or under an inert gas, such as nitrogen. Suitable selective reducing agents are, for example, light metal hydrides, such as dichloroborane, for example in tetrahydrofuran, sodium borohydride, for example in a lower alkanol, or phosphorus(III) compounds, for example phosphorus trichloride or phosphorous acid brenzcatechin phenyl ester, for example in di-, tri or tetrachloromethane. The reduction of the group X may alternatively be carried out by the action of hydrogen in the presence of a suitable hydrogenating catalyst, such as palladium on aluminum oxide, advantageously in a lower alkanol.

The starting materials of the formula II are in some cases known. New compounds of the formula II may be prepared, for example, by converting a compound of the formula

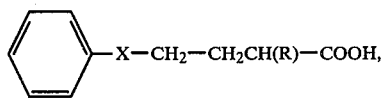

(IIa)

by treating with thionyl chloride in benzene, into the monoacid chloride, reacting this in the presence of diisopropylethylamine and advantageously in toluene as the solvent, with N-acetyl-N,N′-diphenylhydrazine, de-acylating the resulting N-acetylhydrazide by treating with sodium hydroxide solution, and, if desired, liberating the acid from the resulting salt.

The compound of the formula I, in which R represents carboxy, can furthermore be produced as follows: in a compound of the formula III

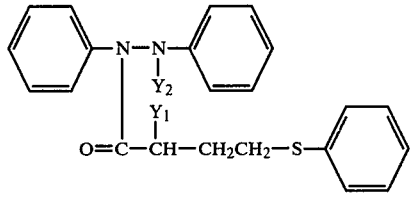

(III)

in which
  $Y_1$ represents a functionally modified carboxy group, and
  $Y_2$ represents hydrogen or an aminoprotecting group, or
  $Y_1$ and $Y_2$ together represent carbonyl,
the functionally modified carboxy group $Y_1$ or the carbonyl group $Y_1 + Y_2$ is solvolysed, with the $Y_2$—N— bond of the latter being split off, if required the protecting group is split off, and if desired the resulting acid is converted into a salt or a resulting salt is converted into the acid or into a different salt.

Functionally modified carboxy is, for example, esterified or amidated carboxy. Suitable esterified carboxy groups are, for example, the esterified carboxy groups mentioned initially as esterified carboxy R or esterified carboxy groups that are different from these. Esterified carboxy groups that are different from esterified carboxy groups R are, for example, phenoxycarbonyl, which may optionally be substituted, for example by lower alkyl, lower alkoxy, halogen and/or nitro; cycloalkylcarbonyl or cycloalkyl-lower alkoxy carbonyl, in which cycloalkyl has 5–7 ring members for example; tetrahydropyranyloxycarbonyl or benzhydryloxycarbonyl; or lower alkoxycarbonyl, substituted by halogen or cyano, such as 2,2,2-trichloroethoxycarbonyl or cyanomethoxycarbonyl. Suitable amines of the formula III are, for example, open-chain amides, such as amides with ammonia or primary or secondary organic amines, such as mono- or di-lower alkylamines or 3-aza, 3-oxa or 3-thia-alkyleneamines.

The solvolysis is carried out in the customary manner, preferably by hydrolysis in the presence of an alkaline hydrolysing agent, advantageously whilst heating, for example at a temperature in the range from approximately 50° to 150° C., and if required in the presence of a water-miscible solvent and/or under an inert gas, such as nitrogen. Alkaline hydrolysing agents are, for example, inorganic bases, such as alkali metal hydroxides or carbonates, for example sodium or potassium hydroxide, sodium or potassium carbonate, or ammonia, preferably in dilute, for example 0.5 N to 2 N, solution, furthermore water-miscible organic amines, for example triethylamine. Water-miscible solvents are, for example, lower alkanols, such as methanol or ethanol, dioxan or tetrahydrofuran.

Some of the functional carboxy derivatives of the acid of the formula I to be used as starting materials are known. New starting materials of the mentioned kind can be prepared by methods known per se. Thus, for example, esters of the same may be obtained, for example, by condensing a corresponding 2-(2-phenylthioethyl)malonic acid semiester in the presence of N,N′-dicyclohexylcarbodiimide in tetrahydrofuran with N,N′-diphenylhydrazine. Open-chain amides can be prepared in an analogous manner, wherein starting materials are corresponding 2-(2-phenylthioethyl)-malonic acid semiamides.

The compounds of the formula I may furthermore be prepared by condensing with one another compounds of the formulae IV and V

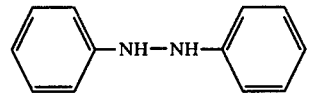

(IV)

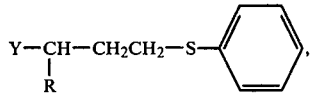

(V)

in which
  Y represents a carboxy group optionally present in anhydride form, and wherein the nitrogen atom of the component IV not participating in the reaction, and/or a carboxy group R optionally present in the component (V) may be present in intermediately protected form,
if required, in the compound which may be obtained in accordance with the process, the protecting group(-groups) is(are) removed, and, if desired, the resulting compound is converted into a different compound of the formula I and/or the optionally resulting compound of the formula I, in which R is carboxy, is converted into a salt, or a resulting salt of such a compound is converted into the free acid or into a different salt.

Carboxy Y present in anhydride form is, for example, halocarbonyl, especially chlorocarbonyl, or, secondly, carboxy anhydridised with a lower alkanecarboxylic acid, for example formyloxycarbonyl, acetoxycarbonyl or pivaloyloxycarbonyl.

The reaction is carried out in a manner known per se, advantageously in a solvent and if required in the presence of a condensing agent, whilst cooling or heating, for example in a temperature range from approximately −20° to 100° C., especially from approximately 0° to 50° C., and/or under an inert gas, such as nitrogen. Suitable solvents are, for example di, tri- and tetra-chloromethane, 1,1,2,2-tetrachloroethane, dioxan, tetrahydrofuran, benzene or toluene. Suitable condensing agents, starting from acid anhydrides, are for example, basic condensing agents, and, starting from acids of the formula V, for example water-binding agents. Basic condensing agents are, for example alkali metal lower alkylates, such as sodium methylate, alkali metal or alkaline earth metal hydroxides or carbonates, for example sodium, potassium or calcium hydroxide or sodium or potassium carbonate, or tertiary organic nitrogen bases, such as tri-lower alkylamines, for example triethylamine or tributylamine, tertiary aniline derivatives, such as N-di-lower alkylanilines, for example N,N-dimethylaniline, or tertiary heterocyclic bases, such as pyridine. Suitable water-binding agents are especially carbodiimides, for example dicyclohexylcarbodiimide.

The starting materials of the formula V are in some cases known. New starting materials may be prepared, for example, starting from the corresponding acid of the formula V, in which Y is carboxy, for example by treating with thionyl chloride, preferably in benzene at approximately 50°, or with a lower alkanoic acid anhydride or chloride, such as the mixed anhydride of formic and acetic acid, acetic anhydride or acetyl chloride, in the presence of an alkali metal or the ammonium salt of the relevant acid.

The compounds of the formula I may furthermore be prepared as follows: in a compound of the formula VI

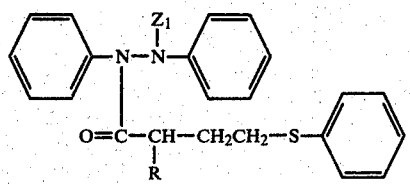

(VI)

in which
Z$_1$ represents a radical that can be split off and in which a carboxy group R may be present in intermediately protected form,
Z$_1$ is split off, if required in the compound which may be obtained in accordance with the process the protecting group is removed, and, if desired, the resulting compound is converted into a different compound of the formula I and/or a resulting compound of the formula I, in which R represents carboxy, is converted into a salt, or a resulting salt of such a compound is converted into the free acid or into a different salt.

The radical Z$_1$ that may be split off is, for example, acyl, such as acyl derived from a carboxylic acid, for example an organic carboxylic acid, or from a carbonic acid semiester, optionally substituted α-phenyl-lower alkyl, sulphonyl or silyl. Acyl derived from an organic carboxylic acid is, for example optionally halogenated lower alkanoyl, such as acetyl, trifluoroacetyl, propionyl or pivaloyl, or benzoyl optionally substituted by lower alkyl, lower alkoxy, halogen and/or nitro. Acyl derived from a carbonic acid semiester is, for example, optionally substituted, such as halogenated, lower alkoxycarbonyl such as methoxycarbonyl, ethoxycarbonyl, 2-iodoethoxycarbonyl, 2,2,2-tribromoethoxycarbonyl, 2,2,2-trichloroethoxycarbonyl or tertiary butoxycarbonyl; 5- to 7-membered cycloalkoxycarbonyl, such as cyclohexyloxycarbonyl; phenyl-lower alkoxycarbonyl, optionally substituted, for example, by lower alkyl, lower alkoxy, halogen and/or nitro, preferably α-phenyl-lowr alkoxycarbonyl, for example benzyloxycarbonyl. Optionally substituted α-phenyl-lower alkyl is, for example, benzyl optionally substituted, for example, by lower alkoxy, halogen and/or nitro. Sulphonyl radicals are, for example, sulphonyl radicals derived from organic sulphonic acids, for example methanesulphonyl, ethanesulphonyl or benzenesulphonyl, p-toluene-sulphonyl or p-bromobenzenesulphonyl. Silyl is, for example, tri-lower alkylsilyl, such as trimethylsilyl.

The splitting off of the radical Z$_1$ is carried out, for example, by solvolysis or reduction. Thus, acyl radicals and silyl radicals Z$_1$ can be split off by hydrolysis and α-phenyl-lower alkyl radicals and α-phenyl-lower alkoxycarbonyl radicals, halogenated lower alkoxycarbonyl radicals and sulphonyl radicals can be split off by reduction.

The solvolysis is carried out in the customary manner, for example by hydrolysis, in the presence of an alkaline hydrolysing agent, advantageously whilst heating, for example in the temperature range of from approximately 50° to 150° C., and is required in the presence of a water-miscible solvent and/or under an inert gas, such as nitrogen. Alkaline hydrolysing agents are, for example, inorganic bases, such as alkali metal hydroxides or carbonates, for example sodium or potassium hydroxide, sodium or potassium carbonate, or ammonia, preferably in dilute, for example 0.5 to 2 N, solution, furthermore water-miscible organic amines, for example triethylamine.

The splitting off by reduction of the radical Z$_1$ is carried out, for example, by the action of a suitable reducing agent, advantageously in an organic solvent that is inert under the reaction conditions, if required whilst cooling or heating, for example in the temperature range of from approximately 0° to approximately 150° C., and/or under an inert gas, such as nitrogen. Reducing agents for the splitting off by reduction of α-phenyl-lower alkyl and α-phenyl-lower alkoxycarbonyl are, for example, hydrogen in the presence of a hydrogenating catalyst, such as a palladium or rhodium catalyst, for example palladium or rhodium on aluminium oxide. In this process variant, it may be especially advantageous to start from a compound of the formula VII, in which R represents α-phenyl-alkoxycarbonyl.

Because this is likewise reduced, namely to carboxy, in this manner the acid of the formula I can be easily obtained. Halogenated lower alkoxycarbonyl radicals and sulphonyl radicals can be split off, for example by treating with zinc in the presence of dilute acetic acid, halogenated lower alkoxycarbonyl radicals may also be split off by reacting with chromium(II) chloride or with chromium(II) acetate, α-phenyl-lower alkoxycarbonyl also by treating with sodium in liquefied ammonia.

The starting materials of the formula VI can be prepared, for example, by reacting a compound of the formula

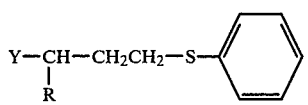

(V)

in which Y represents carboxy optionally present in anhydride form, with an N,N'-diphenyl-N-$Z_1$-hydrazine.

The reaction is carried out in a manner known per se, advantageously in a solvent and, if required, in the presence of a condensing agent, whilst cooling or heating, for example in a temperature range of from approximately $-20°$ to $100°$ C., especially from approximately $0°$ to $50°$ C., and/or under an inert gas, such as nitrogen. Suitable solvents are, for example, di-, tri- and tetrachloromethane, 1,1,2,2-tetrachloroethane, dioxan, tetrahydrofuran, benzene or toluene. Suitable condensing agents are, for example, basic condensing agents, starting from acids of the formula V, for example furthermore water-binding agents. Basic condensing agents are, for example alkali metal lower alkylates, such as sodium methylate, alkali metal or alkaline earth metal hydroxides or carbonates, for example sodium, potassium or calcium hydroxide, or sodium or potassium carbonate, or tertiary organic nitrogen bases, such as tri-lower alkylamines, for example diisopropylamine or tributylamine, tertiary aniline derivatives, such as N,N-di-lower alkylanilines, for example N,N-dimethylaniline, or tertiary heterocyclic bases, such as pyridine. Suitable water-binding agents are especially carbodiimides, for example dicyclohexylcarbodiimide.

The N,N'-diphenyl-N-$Z_1$-hydrazines serving as starting materials for the reaction can be obtained, for example by reacting N,N-diphenyl-hydrazine with a carboxylic acid anhydride, for example acetic anhydride, acetyl chloride or trifluoroacetic anhydride, chloroformic or bromoformic acid esters, for example chloroformic acid benzyl ester, phenyl-lower alkyl halide, for example benzyl bromide, sulphonic acid anhydride, for example p-toluenesulphonechloride or with a tri-lower alkylchlorosilane, for example trimethylchlorosilane.

The compounds of the formula I may furthermore be produced as follows: in a compound of the formula VII

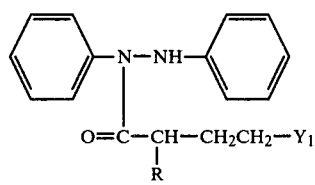

(VII)

in which $Y_1$ represents a radical that may be replaced by the phenylthio group and in which the secondary nitrogen atom and/or a carboxy group R may be present in intermediately protected form, $Y_1$ is replaced by phenylthio, if required in the compound which may be obtained according to the process the protecting group(groups) is(are) removed, and, if desired, the resulting compound is converted into a different compound of the formula I, in which R represents carboxy, into a salt, or a resulting salt of such a compound is converted into the free acid or into a different salt.

The radical $Y_1$ which may be replaced by the phenylthio group is, for example a reactive esterified hydroxy group, such as hydroxy esterified with a halohydric acid or an organic sulphonic acid, for example chlorine, bromine, methanesulphonyloxy or p-bromobenzenesulphonyloxy.

The replacement of $Y_1$ by phenylthio can be carried out in the customary manner, for example by treating with thiophenol or with a salt, such as an alkali metal salt thereof, for example with sodium thiophenolate, advantageously in a solvent that is inert under the reaction conditions, for example an ether, such as diethyl ether, dioxan or tetrahydrofuran, benzene or toluene, or a lower alkanol, such as methanol, if required whilst cooling or heating, for example in a temperature range of from approximately $0°$ to $100°$ C., and/or under an inert gas, such as nitrogen.

The starting materials of the formula VII can be produced, for example, by treating a 2-(2-$Y_1$-ethyl)malonic acid or a semiester thereof or the semichloride thereof in the presence of dicyclohexylcarbodiimide with N,N'-diphenylhydrazine.

As mentioned, functional groups not participating in the above described reactions, namely carboxy groups R in starting materials of the formulae II, V, VI and VII, the secondary aniline nitrogen atom in starting materials of the formulae II, III and VII, and one of the nitrogen atoms in starting materials of the formula IV, may be present in intermediately protected form and are liberated again during, or subsequent to, the actual reaction. Protecting groups are the carboxy-protecting or amino-protecting groups known from chemical literature. Suitable carboxy-protecting groups are especially carboxy-protecting groups bonded ester-fashion, which can be split off in neutral or alkaline medium, and which form esterified carboxy R or phenoxycarbonyl, which may optionally be substituted, for example by lower alkyl, lower alkoxy, halogen and/or nitro, cycloalkylcarbonyl or cycloalkyl-lower alkoxycarbonyl, in which cycloalkyl has for example 5 to 7 ring members, tetrahydropyranyloxycarbonyl or benzhydryloxycarbonyl, or lower alkyloxycarbonyl substituted by halogen or cyano, such as 2,2,2-trichloroethoxycarbonyl or cyanomethyloxycarbonyl. Amino-protecting groups are especially amino-protecting groups that can be split off in neutral or basic medium, for example acyl, such as acyl derived from a carboxylic acid or a carbonic acid semiester, an optionally substituted α-phenyl-lower alkyl, sulphonyl or silyl. An acyl radical that is derived from an organic carboxylic acid is, for example, optionally halogenated lower alkanoyl, such as acetyl, trifluoroacetyl, propionyl or pivaloyl, or benzoyl optionally substituted, for example, by lower alkyl, lower alkoxy, halogen and/or nitro. An acyl radical derived from a carbonic acid semiester is, for example optionally substituted, such as halogenated, lower alkoxycarbonyl, such as methoxycarbonyl, ethoxycarbonyl, 2-iodoethoxycarbonyl, 2,2,2-tribromoethoxycarbonyl, 2,2,2-trichloroethoxycarbonyl, or tertiary butoxycarbonyl, 5- to 7-membered cycloalkoxycarbonyl, such as cyclohexyloxycarbonyl, phenyl-lower alkoxycarbonyl optionally substituted by, for example, lower alkyl, lower alkoxy, halogen and/or nitro, preferably α-phenyl-lower alkoxycarbonyl for example benzyloxycarbonyl. An optionally substituted α-phenyl-lower alkoxycarbonyl is, for example benzyl optionally substituted, for example, by lower alkyl, lower alkoxy, halogen and/or nitro. Sulphonyl radicals are, for example sulphonyl radicals derived from organic sulphonic acids, for example methanesulphonyl, ethanesulphonyl or benzenesulphonyl, p-toluenesulphonyl or p-bromobenzenesulphonyl. A silyl radical is for example, tri-lower alkylsilyl, such as trimethylsilyl. For splitting off the mentioned protecting groups the known methods, for example, those mentioned above, for removing such groups and analogous protecting groups may be considered.

A compound which may be obtained in accordance with the process can be converted into a different compound of the formula I.

Thus, for example, the acids obtainable according to the invention of the formula I, in which R represents carboxy, can be esterified according to customary neutral or basic esterification processes.

Thus, for example, esterification can be effected by treating with a suitable diazo compound, such as a diazo-lower alkane, a suitable N,N-di-lower alkylformamide acetal, for example N,N-dimethylformamide diethyl acetal or N,N,N-trimethylformamide methosulphate, or with an oxonium salt, such as a tri-lower alkyloxonium tetrafluoroborate or hexylfluorophosphate, with a carbonate or pyrocarbonate, for example diethyl(pyro)carbonate, or with an alcohol in the presence of a suitable condensing agent, such as a dehydrating agent, for example dicyclohexylcarbodiimide, or, to form a hydroxy-lower alkyl group, with an epoxy-lower alkane, for example ethylene oxide. Furthermore, a compound of the formula I in which a free carboxyl group R is present in salt form, for example in the alkali metal salt form, such as the sodium salt form, is reacted with a reactive ester of an alcohol, for example a strong acid ester, such as a corresponding halide, for example chloride, bromide or iodide, or sulphuric acid ester; or a compound of the formula I in which R is a carboxyl group can be intermediately protected at the secondary nitrogen atom, then by treating with a halogenating agent, for example thionyl chloride, it can be converted into halocarbonyl, subsequently reacted with a metal alcoholate or an alcohol in the presence of an acid-binding base, the protecting group can be split off, and thus a compound of the formula I is obtained in which R represents esterified carboxy. In that case, substituents optionally present in an esterifying reagent may be present in functionally modified form, and then be liberated in a compound of the formula I, in which R represents, for example, substituted lower alkoxycarbonyl, in which substituents may be present in functionally modified form. Thus, as esterifying reagent there may be used, for example, 2,3-epoxypropyl chloride and in the resulting ester a 2,3-epoxypropoxy group may subsequently be hydrolysed to the desired 2,3-dihydroxypropoxy grouping.

In a compound of the formula I, in which R represents esterified carboxy, for example also p-nitrophenoxycarbonyl or 2,4-dinitrophenoxycarbonyl or p-nitrobenzyloxycarbonyl or 2,4-dinitrobenzyloxycarbonyl, this can be converted by trans-esterification, for example, by treating with an alcohol, if required in the presence of a suitable transesterification catalyst, such as an optionally substituted alkali metal alkylate, for example sodium or potassium alkylate, into a different esterified carboxy group.

In a compound of the formula I in which R represents esterified carboxy, this can be converted in a manner known per se into carboxy, for example by hydrolysis, or, starting from α-phenyl-lower alkyl esters optionally substituted in the phenyl moiety, by reduction.

The hydrolysis is carried out in the customary manner, for example in the presence of an alkaline hydrolysing agent, advantageously whilst heating, for example in the temperature range of from approximately 50° to 150° C., and if required in the presence of a water-miscible solvent and/or under an inert gas, such as nitrogen. Alkaline hydrolysing agents are, for example inorganic bases, such as alkali metal hydroxides or alkali metal carbonates, for example sodium or potassium hydroxide, sodium or potassium carbonate, or ammonia, preferably in dilute, for example 0.5 to 2 N, solution. Furthermore water-miscible organic amines, for example triethylamine.

The reduction is carried out preferably by the action of hydrogen in the presence of a hydrogenating catalyst. Hydrogenating catalysts are, for example, noble metal catalysts, such as palladium or rhodium catalysts, for example palladium or rhodium or aluminium oxide. Advantageously, the reduction is carried out in the presence of a base, such as a tertiary nitrogen base, for example triethylamine, and in a solvent that is inert under the reduction conditions, for example dioxan, if required under excess pressure and/or with gentle heating, for example in the pressure range of from approximately 1 to 5 bar and in the temperature range of from approximately 0° to 5° C. The reduction may alternatively be carried out by treating with sodium in liquefied ammonia.

Resulting free compounds of the formula I can be converted into salts in a manner known per se, for example by treating with the corresponding base, normally in the presence of a solvent or diluent.

Resulting salts can be converted in a manner known per se into the free compounds, for example by treating with an acid, such as an equivalent of a mineral acid.

The compounds of the formula I, including their salts, can also be obtained in the form of their hydrates, or may include the solvent used for the crystallisation.

Owing to the close relationship between the new compound of the formula I, in which R represents carboxy, in free form and in the form of its salts, in the preceding and following text the free compound or its salts shall mean also optionally the corresponding salts or the free compound according to sense and intended use.

The invention also relates to those forms of the process according to which a compound obtainable at any stage of the process as intermediate is used as starting material, and the missing steps are carried out, or a starting material in the form of a salt and/or a racemate or antipode is used, or especially formed under the reaction conditions.

New starting materials and processes for their manufacture are likewise a subject of the present invention.

The pharmaceutical preparations of the invention are those for enteral, such as oral or rectal, as well as parenteral, administration to warm-blooded animals, and which contain the pharmacological active substance alone or together with a pharmaceutically acceptable carrier. The dosage of active substance depends on the species of warm-blooded animal, the age and individual condition, and on the method of administration.

The new pharmaceutical preparations contain, for example, from approximately 10% to approximately 95%, preferably from approximately 20% to approximately 90%, of the active substance. Pharmaceutical preparations of the invention are, for example, those in dosage unit forms, such as dragées, tablets, capsules, suppositories or ampules.

The pharmaceutical preparations according to the present invention are manufactured in a manner known per se, for example by means of conventional mixing, granulating, dragée-making, solubilising or lyophilisation processes.

Thus, pharmaceutical preparations for oral use can be obtained by combining the active substance with solid carriers, optionally granulating a resulting mixture, and processing the mixture or granulate, if desired or necessary after the addition of suitable auxiliaries, to form tablets or dragée cores. Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes, for example of corn, wheat, rice or potato starch pastes, gelatin, tragacanth, methylcellulose and/or polyvinylpyrrolidone, and/or, if desired, disintegrating agents, such as the above-mentioned starches, furthermore carboxymethyl starches, transversely cross-linked polyvinylpyrrolidone, agar, alginic acid or a salt thereof, such as sodium alginate. Auxiliaries are especially flow regulators and lubricants, for example silica, talc, stearic acid or salts thereof, such as magnesium or calcium stearate, and/or polyethyleneglycol. Dragée cores are given suitable coatings, optionally resistant to gastric juice, wherein inter alia concentrated sugar solutions which optionally contain gum arabic, talc, polyvinylpyrrolidone, polyethyleneglycol and/or titanium dioxide are used; lacquer solutions in suitable organic solvents or mixtures of solvents, or, for the manufacture of coatings resistant to gastric juice, solutions of suitable cellulose preparations, such as acetyl cellulosephthalate, or hydroxypropylmethylcellulose phthalate. Colourants or pigments, for example to identify or characterise different doses of active substance, may be added to the tablets or dragée coatings.

Further pharmaceutical preparations for oral administration are push-fit capsules made of gelatin and also soft sealed capsules made from gelatin and a plasticiser, such as glycerin or sorbitol. The push-fit capsules can contain the active ingredient in the form of granules, for example in admixture with fillers, such as lactose, binders, such as starches, and/or lubricants, such as talc or magnesium stearate, and optionally stabilisers. In soft capsules, the active substance is preferably dissolved or suspended in suitable liquids, such as fatty oils, paraffin oil or liquid polyethylene glycols, to which stabilisers may optionally also be added.

Pharmaceutical preparations for rectal administration are e.g. suppositories, which consist of a combination of the active substance with a suppository base. Examples of suitable suppository bases are natural or synthetic triglycerides, paraffin hydrocarbons, polyethylene glycols or higher alkanols. Gelatin rectal capsules, which consist of a combination of the active ingredient with a base material, can also be employed; suitable base materials are e.g. liquid triglycerides, polyethylene glycols or paraffin hydrocarbons.

For parenteral administration there are especially suitable aqueous solutions of an active substance in water-soluble form, for example a water-soluble salt, also suspensions of the active substance, such as corresponding oily injection suspensions, using suitable lipophilic solvents or vehicles, such as fatty oils, for example sesame oil, or synthetic fatty acid esters, for example ethyl oleate or triglycerides, or aqueous injection suspensions, which contain substances increasing viscosity, for example sodium carboxymethylcellulose, sorbitol and/or dextrane and optionally also stabilisers.

The invention likewise relates to the use of the new compounds of the formula I and its salts as medicaments, especially as antithrombotic agents, preferably in the form of pharmaceutical preparations. The daily dosage recommended for a warm-blooded animal of approximately 75 kg body weight is approximately 0.1 to 1 g, preferably from 0.25 to 0.75 g, advantageously divided into 3 or 4 equal daily doses.

The following Examples illustrate the above-described invention; they are not, however, intended to restrict its scope in any way. Temperatures are given in degrees Centigrade.

EXAMPLE 1

A solution of 3.88 g of 1,2-diphenyl-4-(2-phenylthioethyl)pyrazolidin-3,5-dione in 10.25 ml of sodium hydroxide solution is refluxed for 23 hours under nitrogen at a bath temperature of 140°. 5 ml of water are added to the reaction mixture and the whole is refluxed for a further 23 hours. The suspension is then cooled to room temperature, and filtered. 2 N hydrochloric acid is added to the filtrate until Congo paper turns blue, and it is then extracted twice with 50 ml of ethyl acetate each time. The combined organic phases are washed twice with 20 ml of water each time, dried over magnesium sulphate, and concentrated by evaporation at a bath temperature of 40° under reduced pressure. The residue, a yellow oil, is dissolved in 50 ml of ethyl acetate, the solution is extracted twice with 25 ml of 2 N potassium bicarbonate solution each time and then twice with 50 ml of 0.5 N sodium carbonate solution each time. The sodium carbonate solutions are combined, and acidified with concentrated hydrochloric acid at 5°. The oil that precipitates is extracted twice with 50 ml of ethyl acetate each time. The combined organic phases are washed with 20 ml of water, dried over magnesium sulphate, and evaporated to dryness under reduced pressure at a bath temperature of 40°. The residue, an oil, is chromatographed on 500 g of silica gel. Fractions 1 to 14, each eluted with 200 ml of toluene, and fractions 15 to 18, each eluted with 200 ml of toluene-ethyl acetate, are discarded. Fractions 19 and 20, each eluted with 200 ml of toluene-ethyl acetate, are combined and concentrated by evaporation in vacuo. The residue is dissolved in 50 ml of acetone. The ethereal solution has petroleum ether added to it until it turns turbid. After standing for a while, 2-(2-phenylthioethyl)-malonic acid monoethyl ester-N,N'-diphenyl hydrazide crystallise out as a colourless crystal. Mp. 82°–84°.

EXAMPLE 2

At 5°–10°, a solution of 17.9 g of dicyclohexylcarbodiimide in 95 ml of absolute tetrahydrofuran is added dropwise under nitrogen to a solution of 22.9 g of 2-(2-phenylthioethyl)malonic acid monoethylester and 15.7 g of freshly recrystallised hydrazobenzene in 160 ml of absolute tetrahydrofuran. Thereupon the mixture is stirred under nitrogen for 15 hours at 25°, then the dicyclohexylurea that has precipitated is filtered off, and the filtrate is evaporated to dryness in vacuo after the addition of three drops of glacial acetic acid. The residue is dissolved in 1 liter of ether, the ethereal solution is extracted twice with 100 ml of 2 N potassium bicarbonate solution each time and twice with 100 ml of 2 N hydrochloric acid each time, and then washed until neutral with water. The ethereal solution is then dried over sodium sulphate, and concentrated in vacuo. The residue, an oil, is chromatographed on 500 g of silica gel. Fractions 1 to 14 each eluted with 200 ml of toluene, and fractions 15 to 18, each eluted with 200 ml of toluene-ethyl acetate, are discarded. Fractions 19 and 20, each eluted with 200 ml of toluene-ethyl acetate, are combined and concentrated by evaporation in vacuo. The residue is dissolved in 50 ml of ether. Petroleum ether is added to the ethereal solution until it turns turbid. After standing for a while, 2-(2-phenylthioethyl)malonic acid monoethylester-N,N'-diphenyl hydrazide crystallises out as colourless crystals. Mp. 82°–84°.

EXAMPLE 3

A suspension of 8.9 g of 2-(2-phenylthioethyl)malonic acid monoethylester-N,N'-diphenyl hydrazide in 40 ml of aqueous 0.5 N sodium hydroxide solution is refluxed for 12 hours under nitrogen. The solution is filtered, and freed from traces of hydrazobenzene by extracting with ether. The aqueous solution is acidified at 10° with concentrated hydrochloric acid until Congo paper turns blue, the oil that precipitates is dissolved in 40 ml of ethyl acetate, the solution is separated off and washed until neutral with water. The solution is then extracted twice with 36 ml of 0.5 N sodium carbonate solution each time. The extracts are separately acidified with concentrated hydrochloric acid until Congo paper turns blue, extracted with ethyl acetate, the extracts are washed with a little water until neutral, dried and concentrated by evaporation in vacuo. The residual colourless oil is recrystallised twice from ethyl acetate (acetic ester), 2-(2-phenylthioethyl)malonic acid N,N'-diphenyl monohydrazide being obtained. Mp. 158°–160°.

0.5 g of 2-(2-phenylthioethyl)malonic acid monobenzylester-N,N'-diphenyl hydrazide is dissolved in 40 ml of methanol, and after the addition of 0.4 g of palladium on aluminium oxide (5%), is hydrogenated at room temperature and normal pressure. After 13 hours, a further 0.2 g of catalyst is added and after a total of 24 hours the hydrogenation is broken off. The catalyst is filtered off, and the filtrate is evaporated to dryness under reduced pressure. The residue is dissolved in 15 ml of ethyl acetate. The organic phase is extracted twice at 0° with 10 ml of 2 N sodium carbonate solution each time. The combined aqueous-alkaline solutions are acidified with 2 N hydrochloric acid. The oil that precipitates is extracted with 20 ml of chloroform and the chloroform extract is dried over magnesium sulphate and concentrated by evaporation under reduced pressure. The residue is chromatographed on 20 g of silica gel. Fractions 1 to 7, each eluted with 50 ml of chloroform-methanol (9:1), are discarded. Fractions 8 to 10, eluted with the same mixture, are combined and evaporated to dryness under reduced pressure. The residue is crystallised from ethyl acetate. The 2-(2-phenylthioethyl)malonic acid N,N'-diphenyl hydrazide melts at 158°–160°.

The starting material may be obtained as follows: 4.8 g of a sodium hydride-mineral oil dispersion (50%) are added in portions at 0°, over the course of 45 minutes, to a solution of 28.4 g of malonic acid dibenzyl ester in 150 ml of dimethylformamide, whilst stirring and with the exclusion of moisture. The mixture is stirred for 2 hours at room temperature, and then a solution of 2-phenylthioethyl bromide in 50 ml of dimethylformamide is added dropwise. The mixture is then stirred for 20 hours at 50°, cooled and poured into 1.5 liters of ice water. The oil that precipitates is dissolved by extracting twice with 500 ml of ether each time. The combined ether solutions are washed with 200 ml of water, dried over magnesium sulphate, and concentrated by evaporation under reduced pressure. The residue is chromatographed on 1000 g of silica gel. Fractions 1–4, each eluted with 500 ml of toluene, are discarded. Fractions 5–25 contain 2-(2-phenylthioethyl)malonic acid dibenzyl ester. The fractions are combined, and evaporated to dryness under reduced pressure. The ester is a colourless oil.

21.2 g of 2-(2-phenylthioethyl)malonic acid dibenzyl ester are dissolved in 70 ml of dioxan. The solution is heated to 70°, and, whilst stirring, 50.5 ml of 1 N sodium hydroxide solution are added. Stirring is continued for 20 minutes at 70°, the mixture is cooled and the dioxan is distilled off at 40° under reduced pressure. The aqueous solution is covered with a layer of 100 ml of ether and acidified at 0° with 35 ml of 2 N hydrochloric acid. The ether phase is separated off and the aqueous phase extracted twice with 100 ml of ether each time. The combined ether phases are extracted with 100 ml of 0.5 N potassium bicarbonate solution and then three times with 50 ml of 2 N sodium carbonate solution each time. The combined sodium carbonate solutions are acidified at 0° with 2 N hydrochloric acid. The oil that precipitates is dissolved by extracting three times with 60 ml of chloroform each time. The combined chloroform solutions are dried over magnesium sulphate and concentrated by evaporation under reduced pressure. The residue is dried for 15 hours at room temperature at 0.1 torr. 2-(2-Phenylthioethyl)malonic acid monobenzyl ester is obtained as a colourless oil.

A solution of 4.8 g of 2-(2-phenylthioethyl)malonic acid monobenzyl ester in 30 ml of anhydrous tetrahydrofuran is cooled, whilst stirring and with the introduction of nitrogen, to 0°. 2.7 g of hydrazobenzene and then dropwise a solution of 3.05 g of dicyclohexylcarbodiimide in 15 ml of anhydrous tetrahydrofuran are then added. The mixture is stirred for 15 hours at room temperature and suctionfiltered. The filtrate has 3 drops of glacial acetic acid added to it and is evaporated to dryness under reduced pressure. The residue is dissolved in 150 ml of ether. The ether phase is extracted twice with 25 ml of 2 N hydrochloric acid each time, twice with 25 ml of 2 N sodium bicarbonate solution and then with 30 ml of water, dried over magnesium sulphate and evaporated to dryness under reduced pressure. The residue is chromatographed on 120 g of silica gel. Fractions 1–4, each eluted with 200 ml of toluene, and fractions 5–6, each eluted with 100 ml of toluene-ethyl acetate (9:1), are discarded. Fractions 7–9, each eluted with 100 ml of toluene-ethyl acetate (9:1), are combined and evaporated to dryness under reduced pressure. The residue is crystallised from diethyl ether/- petroleum ether. The 2-(2-phenylthioethyl)malonic acid monobenzyl ester N,N'-diphenyl hydrazide melting at 88°–89° is obtained.

EXAMPLE 4

0.5 g of 2-(2-phenylthioethyl)malonic acid monobenzyl ester N,N'-diphenyl hydrazide is dissolved in 40 ml of methanol and after the addition of 0.4 g of palladium on aluminium oxide (5%) is hydrogenated at room temperature and normal presure. After 12 hours a further 0.2 g of catalyst is added and after a total of 24 hours the hydrogenation is broken off. The catalyst is filtered off and the filtrate evaporated to dryness under reduced pressure. The residue is dissolved in 15 ml of ethyl acetate. The organic phase is extracted twice at 0° with 10 ml of 2 N sodium carbonate solution each time. The combined aqueous-alkaline solutions are acidified with 2 N hydrochloric acid. The oil that precipitates is extracted with 20 ml of chloroform and the chloroform extract is dried over magnesium sulphate and concentrated by evaporation under reduced pressure. The residue is chromatographed on 20 g of silica gel. Fractions 1–7, each eluted with 50 ml of chloroform-methanol (9:1), are discarded. Fractions 8–10, eluted with the same mixture, are combined and evaporated to dryness under reduced pressure. The residue is crystallised from ethyl acetate. The 2-(2-phenylthioethyl)malonic acid N,N'-diphenyl hydrazide melts at 158°–160°.

EXAMPLE 5

A solution of 4.76 g of 2-(2-phenylthioethyl)malonic acid monoethyl ester N'-acetyl-N,N'-diphenyl hydrazide (mp. 76°–78°, DOS 2 023 415) in 100 ml of ethanol and 10.0 ml of 1 N sodium hydroxide solution is stirred for 3 hours at room temperature and the ethanol is then distilled off at 40° under reduced pressure. The aqueous residue is diluted with 50 ml of water and then extracted twice with 40 ml of methylene chloride each time. The methylene chloride solution, which contains the sodium salt of the desired compound, is separated off and extracted twice with 20 ml of 2 N sodium carbonate solution each time. The sodium carbonate solutions are combined, and rendered acidic with 2 N hydrochloric acid at 5°. The oil that precipitates is dissolved in 60 ml of methylene chloride, the methylene chloride solution is dried over magnesium sulphate, and evaporated to dryness at a bath temperature of 40°. The residue is crystallised from ethanol. The 2-(2-phenylthioethyl)malonic acid N'-acetyl-N,N'-diphenyl hydrazide melts at 159°–161°.

EXAMPLE 6

A solution of 1.8 g of 2-(2-phenylthioethyl)malonic acid N'-acetyl-N,N'-diphenyl hydrazide in 22 ml of 0.5 N sodium hydroxide solution is heated for 15 hours at 60° whilst stirring. The mixture is cooled and the oil that has precipitated is dissolved by adding 20 ml of water. The aqueous phase is extracted three times with 20 ml of toluene each time and then acidified with 2 N hydrochloric acid (pH 1). The oil that precipitates is extracted three times with 60 ml of chloroform each time. The combined chloroform solutions are dried over magnesium sulphate, filtered off and evaporated to dryness at 40° under reduced pressure. After crystallisation from ethyl acetatehexane, the 2-(2-phenylthioethyl)malonic acid N,N'-diphenyl hydrazide melts at 158°–160°.

EXAMPLE 7

0.4 g of 2-(2-phenylthioethyl)malonic acid N,N'-diphenyl monohydrazide is dissolved in 1.0 ml of N sodium hydroxide solution. The solution is diluted with 3 ml of water and, whilst stirring, 73.5 mg of calcium chloride dihydrate are added. The crystals that precipitate are filtered off and washed with 4.0 ml of water. The calcium salt melts at 143°–147°.

EXAMPLE 8

A solution of 3.0 g of 2-(2-phenylthioethyl)malonic acid monoethylester N'-acetyl-N,N'-diphenyl hydrazide (mp. 76°–78°) in 20 ml of ethanol and 15 ml of 1 N sodium hydroxide solution is refluxed for 2 hours and then the alcohol is distilled off at 50° under reduced pressure. 20 ml of water are added, the mixture is cooled to 10°, filtered, the filtrate is acidified at 5° with 2 N hydrochloric acid and the oil that has precipitated is extracted twice with 40 ml of ethyl acetate each time. The combined organic phases are washed twice with 10 ml of water each time, dried over magnesium sulphate and evaporated to dryness at a bath temperature of 40° under reduced pressure. The residue, 2-(2-phenylthioethyl)malonic acid N,N'-diphenyl monohydrazide melts at 158°–160°.

EXAMPLE 9

Lacquer-coated tablets containing 0.25 g of 2-(2-phenylthioethyl)malonic acid N,N'-diphenyl monohydrazide may be manufactured as follows:

| Composition (for one tablet) | |
| --- | --- |
| 2-(2-phenylthioethyl)malonic acid N,N'-diphenyl monohydrazide | 0.300 g |
| corn starch | 0.088 g |
| colloidal silica | 0.020 g |
| magnesium stearate | 0.002 g |
| stearic acid | 0.005 g |
| sodium carboxymethyl starch | 0.025 g |
| water | q.s |

The lacquer coated tablets are manufactured as follows (for 10,000 tablets).

The mixture of 3.0 kg of 2-(2-phenylthioethyl)-malonic acid N,N'-diphenyl monohydrazide and 200 g of colloidal silica is processed with a starch paste of 450 g of corn starch and 2.2 kg of de-mineralised water to a moist composition. This is forced through a sieve of 3 mm mesh width and dried at 45° for 30 minutes in a fluidised bed drier. The dry granulate is pressed through a sieve of 1 mm mesh width, mixed with a previously sieved mixture (1 mm mesh sieve) of 130 g of corn starch, 20 g of magnesium stearate, 50 g of stearic acid and 250 g of sodium carboxymethyl starch and compressed to slightly arched tablets of 6 mm diameter (with breaking groove).

The tablets manufactured according to the above process are given a lacquer coating as follows:

The pressed tablets are coated in a dragée keetle of 45 mm diameter with a solution of 20 g of shellac and 40 g of hydroxypropylmethylcellulose (low viscosity) in 110 g of methanol and 1350 g of methylene chloride by uniform spray application over 30 minutes; by simultaneous admission of air at 60°, the coatings are dried.

Instead of 2-(2-phenylthioethyl)malonic acid N,N'-diphenyl monohydrazide, the corresponding amount of one of its salts, for example the sodium salt, may also be used.

EXAMPLE 10

Tablets containing 0.25 g of 2-(2-phenylthioethyl)-malonic acid N,N'-diphenyl monohydrazide or the corresponding amount of its sodium salt, may be manufactured, for example as follows:

| Composition (for one tablet) | |
|---|---|
| 2-(2-phenylthioethyl)malonic acid N,N'-diphenyl monohydrazide | 250 mg |
| lactose | 100 mg |
| wheat starch | 200 mg |
| colloidal silica | 24 mg |
| magnesium stearate | 4 mg |
| talc | 22 mg |
| water | q.s. |

The tablets are manufactured in the following manner:

The active substances are mixed with a part of the wheat starch, with the lactose and the colloidal silica and the mixture is forced through a sieve. A further portion of the wheat starch is made into a paste on a water bath with five times the amount of water and the above powder mixture is kneaded with this paste until a slightly plastic composition has formed. The plastic composition is pressed through a sieve of approximately 3 mm mesh width, dried, and the dry granulate is again forced through a sieve. The remaining wheat starch, the talc and the magnesium stearate are admixed, and the resulting mixture is compressed to form slightly arched tablets of 0.6 g (with breaking groove).

EXAMPLE 11

Dragées, containing 0.25 g of 2-(2-phenylthioethyl)-malonic acid N,N'-diphenyl monohydrazide or a salt thereof, for example the sodium salt, can be manufactured, for example, in the following manner:

1000 g of the tablets obtainable according to Example 7 are made into dragées with a sugar-containing syrup in the customary manner in two stages. In the first stage a syrup is obtained from one part sugar and two parts water with the addition of talc (18%), polyvinylpyrrolidone (1.5%) and polyethyleneglycol 6000 (1%), and in the second stage a pure sugar syrup is used.

EXAMPLE 12

Tablets containing 0.1 g of the active substance, for example 2-(2-diphenylthioethyl)malonic acid N,N'-diphenyl monohydrazide or a salt, for example the sodium salt thereof, may be manufactured, for example in the following composition:

| Composition | per tablet |
|---|---|
| active substance, e.g. 2-(2-phenylthioethyl)malonic acid N,N'-diphenyl monohydrazide | 100 mg |
| lactose | 50 mg |
| wheat starch | 73 mg |
| colloidal silica | 13 mg |
| talc | 12 mg |
| magnesium | 2 mg |
| | 250 mg |

Manufacture

The active substance is mixed with the lactose, a part of the wheat starch and with the colloidal silica, and the mixture is forced through a sieve. A further portion of the wheat starch is made into a paste on a water bath with 5 times the amount of water and the powder mixture is kneaded with this paste until a slightly plastic composition has formed. The composition is forced through a sieve of approximately 3 mm mesh width, dried and the dry granulate is again forced through a sieve. The remaining wheat starch, the remaining talc and the remaining magnesium stearate are added. The resulting mixture is compressed to form tablets of 0.25 g having breaking groove(s).

EXAMPLE 13

Pharmaceutical preparations containing a different compound of the formula I, preferably one of those mentioned in Examples 1 to 8, as the active substance may also be manufactured in a manner analogous to that described in Examples 7 to 12.

What is claimed is:

1. A new carboxylic acid hydrazide of the formula

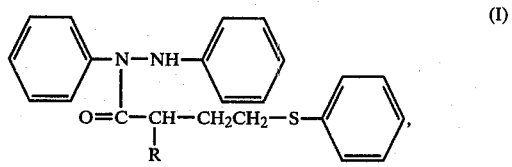

in which

R represents carboxy, or a pharmaceutically acceptable salt of the compound of the formula I.

2. 2-(2-Phenylthioethyl)malonic acid benzyl ester N,N'-diphenyl hydrazide.

3. A pharmaceutical preparation containing an antithrombotically effective amount of a carboxylic acid hydrazide of the formula

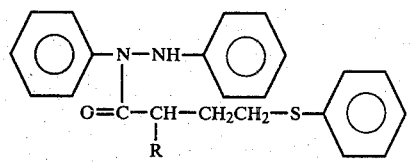

wherein R represents carboxy or a pharmaceutically acceptable salt thereof, lower alkoxycarbonyl or phenyl-lower alkoxycarbonyl, together with one or more pharmaceutically acceptable carriers.

* * * * *